United States Patent
Kim et al.

(10) Patent No.: US 11,737,973 B2
(45) Date of Patent: Aug. 29, 2023

(54) MICRONEEDLE PERCUTANEOUS PATCH CONTAINING DONEPEZIL

(71) Applicant: RAPHAS CO., LTD., Seoul (KR)

(72) Inventors: Tae Hyung Kim, Gyeonggi-do (KR); Booyong Lee, Seoul (KR); Jung Dong Kim, Seoul (KR); Do Hyeon Jeong, Seoul (KR); Dongchul Shin, Gyeonggi-do (KR); Yongyoun Hwang, Gyeonggi-do (KR); Yun-Sun Nam, Gyeonggi-do (KR); Joo Han Lee, Gyeonggi-do (KR); Eun Jin An, Seoul (KR)

(73) Assignee: Raphas Co., Ltd., Seoul (KR)

( * ) Notice: Subject to any disclaimer, the term of this patent is extended or adjusted under 35 U.S.C. 154(b) by 407 days.

(21) Appl. No.: 16/614,527

(22) PCT Filed: May 16, 2018

(86) PCT No.: PCT/KR2018/005614
§ 371 (c)(1),
(2) Date: Nov. 18, 2019

(87) PCT Pub. No.: WO2018/212592
PCT Pub. Date: Nov. 22, 2018

(65) Prior Publication Data
US 2020/0179272 A1 Jun. 11, 2020

(30) Foreign Application Priority Data
May 19, 2017 (KR) .......................... 10-2017-0062465

(51) Int. Cl.
*A61M 37/00* (2006.01)
*A61K 9/00* (2006.01)
(Continued)

(52) U.S. Cl.
CPC .......... *A61K 9/0021* (2013.01); *A61K 31/445* (2013.01); *A61K 47/36* (2013.01); *A61M 37/0015* (2013.01); *A61M 2037/0023* (2013.01)

(58) Field of Classification Search
CPC .... A61K 9/0021; A61K 31/445; A61K 47/36; A61K 9/7023; A61K 9/703; A61K 9/00;
(Continued)

(56) References Cited

U.S. PATENT DOCUMENTS

| 2004/0258741 A1 | 12/2004 | Terahara et al. |
| 2008/0138388 A1 | 6/2008 | Aida et al. |

(Continued)

FOREIGN PATENT DOCUMENTS

| CN | 106422045 A | * | 2/2017 |
| CN | 106422045 A | | 2/2017 |

(Continued)

OTHER PUBLICATIONS

EP Extended European Search Report in European Appln. No. 18801678.6, dated Nov. 24, 2020, 11 pages.
(Continued)

*Primary Examiner* — Amber R Stiles
(74) *Attorney, Agent, or Firm* — Fish & Richardson P.C.

(57) ABSTRACT

The present invention relates to a composition for preparing a microneedle, a soluble microneedle, and a microneedle percutaneous patch comprising the soluble microneedle. A soluble microneedle contained in a microneedle percutaneous patch of the present invention has a high drug loading capacity and excellent strength and thus may contain an effective amount of donepezil or a pharmaceutically acceptable salt thereof even with a small area of the microneedle. Accordingly, the present invention is economical and produces a lower level of skin irritation.

13 Claims, 8 Drawing Sheets

(51) Int. Cl.
*A61K 31/445* (2006.01)
*A61K 47/36* (2006.01)

(58) Field of Classification Search
CPC ............... A61K 9/70; A61M 37/0015; A61M 2037/0023; A61M 31/00; A61M 37/00
See application file for complete search history.

(56) References Cited

U.S. PATENT DOCUMENTS

| | | | |
|---|---|---|---|
| 2008/0213461 A1* | 9/2008 | Gill | A61K 9/0021 427/2.3 |
| 2009/0175929 A1 | 7/2009 | Terahara et al. | |
| 2010/0080842 A1 | 4/2010 | Wen et al. | |
| 2010/0280457 A1* | 11/2010 | Tokumoto | B81C 1/00206 604/173 |
| 2011/0288485 A1* | 11/2011 | Tokumoto | A61K 9/0021 604/173 |
| 2012/0330250 A1 | 12/2012 | Kuwahara et al. | |
| 2013/0041330 A1 | 2/2013 | Matsudo et al. | |
| 2015/0141910 A1* | 5/2015 | Francis | A61M 37/0015 264/255 |
| 2019/0160272 A1* | 5/2019 | Gu | A61M 37/00 |

FOREIGN PATENT DOCUMENTS

| | | |
|---|---|---|
| EP | 2653186 | 10/2013 |
| JP | 2010-082401 A | 4/2010 |
| JP | 2012-158607 A | 8/2012 |
| JP | 2015-151380 | 8/2015 |
| JP | 2016-175853 | 10/2016 |
| KR | 10-2012-0138235 A | 12/2012 |
| KR | 10-2014-0051648 A | 5/2014 |
| KR | 10-2016-0074433 A | 6/2016 |
| KR | 10-2016-0112975 A | 9/2016 |
| KR | 10-2016-0145470 A | 12/2016 |
| KR | 10-2016-0145475 A | 12/2016 |
| KR | 10-2017-0008183 A | 1/2017 |
| KR | 10-1719319 B1 | 3/2017 |
| RU | 2428179 | 9/2011 |
| RU | 2450805 | 5/2012 |
| RU | 2562885 | 9/2015 |
| WO | WO 2007/064407 | 6/2007 |
| WO | WO 2007/129427 | 11/2007 |
| WO | WO 2009/060473 | 5/2009 |
| WO | 2011/049038 A1 | 4/2011 |
| WO | WO 2011/135533 | 11/2011 |

OTHER PUBLICATIONS

JP Office Action in Japanese Appln. No. 2020-514481, dated Oct. 5, 2020, 11 pages (with English Translation).

International Search Report for PCT/KR2018/005614 dated Aug. 29, 2018. 3 pages.

Kim, Jung Dong et al., "Droplet-born Air Blowing: Novel Dissolving Microneedle Fabrication", Journal of Controlled Released, 2013, vol. 170, pp. 430-436.

Kim, Ji-Yeong et al., "Tip-loaded Dissolving Microneedles for Transdermal Delivery of Donepezil Hydrochloride for Treatment of Alzheimer's Disease", European Journal of Pharmaceutics and Biopharmaceutics, 2016, vol. 105, pp. 148-155.

Kearney et al., "Microneedle-mediated delivery of donepezil: Potential for improved treatment options in Alzheimer's disease," European Journal of Pharmaceutics and Biopharmaceutics, 2016, 103:43-50.

RU Office Action in Russian Appln. No. 2019142004, dated Feb. 17, 2020, 13 pages (English translation).

RU Search Report in Russian Appln. No. 2019142004, dated Feb. 17, 2020, 6 pages (English translation).

JP Office Action in Japanese Appln. No. 2020-514481, dated Jan. 11, 2022, 13 pages (with English Translation).

KR Notice of Allowance in Korean Appln. No. 10-2017-0062465, dated Oct. 4, 2019, 6 pages (with Machine Translation).

KR Office Action in Korean Appln. No. 10-2017-0062465, dated Jan. 29, 2019, 12 pages (with Machine Translation).

Okamoto, "Hyaluronic Acid and Joint Fluid," Journal of Biorheology Society (B&R) in Japan, 1999, 13(4):168-174, 21 pages (with English Translation).

* cited by examiner

Example 1

Example 2

Example 3

Example 4

MICRONEEDLE PERCUTANEOUS PATCH CONTAINING DONEPEZIL

CROSS-REFERENCE TO PRIOR APPLICATION

This is the U.S. National Phase Application under 35 U.S.C. § 371 of International Patent Application No. PCT/KR2018/005614 filed May 16, 2018, which claims the benefit of Korean Patent Application No. 10-2017-0062465 filed May 19, 2017, both of which are incorporated by reference herein. The International Application was published in Korean on Nov. 22, 2018 as WO2018/212592 A1 under PCT Article 21(3).

TECHNICAL FIELD

The present invention relates to a composition for preparing a microneedle comprising donepezil, a soluble microneedle for percutaneous delivery of donepezil, and a microneedle percutaneous patch containing the soluble microneedle.

BACKGROUND

Dementia refers to a syndrome characterized by complex cognitive disorders which feature loss of memory, regression of intelligence, change of personality, speech disorder, behavioral abnormalities, etc. With a growing aged population in modern society, patients with dementia of Alzheimer's type have been increased in number, and thus the management of such patients has emerged as a serious social issue. A cause of dementia has not been clarified yet, but it is known that a concentration of a neurotransmitter, i.e., acetylcholine in brain is decreased by about 16-30% in patients with dementia compared to normal people. It is also known that the cognitive ability of the patients with dementia of Alzheimer's type may be enhanced by increasing the acetylcholine in brain. Accordingly, a method for increasing the concentration of acetylcholine by using a factor for acetylcholine decomposition, i.e., an acetylcholinesterase inhibitor has been widely used in the treatment of the patients with dementia.

Donepezil, one of the acetylcholinesterase inhibitors, has been sold as an oral preparation at a dose of 5 mg, 10 mg or 23 mg, which is administered once a day, and is used in the treatment of mild and moderate or severe degree of dementia caused by Alzheimer's disease. However, most of the patients with dementia are elderly people, who have difficulty in swallowing an oral preparation. Also, in many cases, those elderly people may not be able to remember whether they have taken medicine or not due to cognitive disorders such as loss of memory, etc., and thus there is a problem of decrease in their adherence to medication.

A percutaneous absorption preparation may be one of the solutions to such problems of the patients with dementia. A matrix form of donepezil percutaneous absorption-type preparation has been disclosed in the U.S. Patent Publication No. 2004/0258741, No. 2010/0080842, No. 2008/0138388, No. 2009/0175929 and International Patent Publication WO 2011/049038. However, donepezil hydrochloride has a molecular weight of 415.96 and log P of 4.27, which result in physicochemical properties close to a limit of possible percutaneous penetration (molecular weight of 500, lop 5 or less), and thus does not penetrate skin well. For that reason, a conventionally general matrix form of donepezil percutaneous absorption preparation must be prepared with an excessively large area in order to overcome such a low skin penetration rate. Furthermore, there is a problem in that the percutaneous absorption preparation must carry donepezil at least dozens of times more than a dose used in the oral preparation.

To overcome such problems, new systems such as iontophoresis, electrophoresis, heating, microneedle, etc., have been developed. Out of those systems, the microneedle has an advantage in that it may be applied in a form of patch without any accessory equipment and thus may be easily applied in daily life. A microneedle patch works in such a manner that a number of microneedles are attached to an inside of the patch and bore tiny holes into skin surface to deliver a drug thereinto. The needle patch in a microunit may deliver the drug with a little or no pain compared to injection preparations. However, due to a limit in an amount of loading capacity of drug per unit area, etc., most concentration has been put on the development of high potency drugs (for example, vaccine, bio-drugs, etc.), which may expect an effect with a less dose.

To overcome the limit in the drug loading capacity of such microneedle patch, attempts have been made to have a matrix or film type of drug depot on the back side thereof and have a hydrogel type of microneedle on the front side thereof, and thus the hydrogel microneedle may penetrate skin and then swell enough to serve as a pathway, through which the drug may be diffused and delivered into the skin. However, such method has a disadvantage in that the drug is released simply by diffusion, and thus a delivery rate thereof becomes low and the drug also causes irritation to skin due to expansion of the needle.

As a result of conducting an in vitro test with the hydrogel type of microneedle, out of 2 mg of the donepezil loading capacity, a delivery rate for 24 hours was just a level of about 10 to 34% and it was required to carry a dose of 160 mg, which was at least 10 times higher than an oral dosage (5 mg/10 mg). Also, the drug loading capacity per area of a corresponding group is 0.08 mg/cm$^2$. Thus, it is required to attach a patch having an area of about 188 to 1,250 cm$^2$. However, the attachment of such a large patch to skin for a long time may cause many problems such as skin inflammations, etc. Thus, a technology for maximizing the drug loading capacity per unit area needs to be developed yet such that an oral drug at a dose of several mg to dozens of mg/day may be developed at a commercially available level of patch type. However, an amount of polymer material, which forms the microneedle, is decreased according to an increase in the drug loading capacity, which results in being accompanied by a decrease in the strength of the microneedle. Thus, there occurs a problem in that such decrease leads to a decrease in an insertion capacity to penetrate skin, which is the nature of the microneedle functions. Meanwhile, an increase in the drug loading capacity may be achieved to some degree by increasing the number of microneedles per area, that is, a degree of integration. However, an interval between microneedles becomes narrow according to an increase in the degree of integration, and thus there occurs a decline in the insertion capacity, which is also named a bed nail effect. Such decrease in the insertion capacity leads to a decrease in the delivery rate of the drug into skin.

Thus, there is a need for the microneedle, which uses a less dose of the drug by raising a skin penetration rate, and has the strength enough to penetrate skin even with an increase in the drug loading capacity of the microneedle, while having a less skin contact surface area.

DETAILED DESCRIPTION OF THE INVENTION

Technical Problem

An objective of the present invention is to provide a composition for preparing a microneedle, in order to prepare the microneedle, which maintains an appropriate strength for penetrating skin, while having a high drug loading capacity.

Also, an objective of the present invention is to provide a soluble microneedle, which maintains an appropriate strength for penetrating skin, while having a high drug loading capacity.

Furthermore, an objective of the present invention is to provide a microneedle percutaneous patch comprising the soluble microneedle.

Technical Solution

In order to achieve the objectives above, the present invention provides i) a composition for preparing a microneedle, 2) a soluble microneedle, and 3) a microneedle percutaneous patch.

As used herein, the term "microneedle" means a needle-shaped structure having a length of micrometer (μm) unit, in which a tip thereof takes on such a pointed shape as a needle and thus may penetrate skin. A structure thereof is referred to FIG. 1. The microneedle forms a hole in an outer-most layer of skin, i.e., a keratin layer, and thus delivers a drug through the hole formed therein. The microneedle has a very short length, which is appropriate enough not to have an influence on nerve cells, thus causing almost no pains.

As used herein, the term "soluble (dissolving) microneedle" means a microneedle, which is dissolved in vivo and thus releases the drug carried thereby when being applied for skin penetration. Not a soluble, but a hydrogel type of microneedle swells when penetrating skin, and thus may give pressure into skin to cause irritation, and also may generate pains during a removal process thereof. However, the soluble microneedle becomes extinct after being applied onto skin, and thus causes less irritation to skin and without a need for removal.

As used herein, the term "patch" means a dosage form which is attached onto skin to deliver the drug into the body, in which a structure thereof is referred to FIG. 2.

Hereinafter, each of the inventions will be taken into consideration in detail.

Composition for Preparing Microneedle

The present invention provides a composition for preparing a microneedle, comprising donepezil or a pharmaceutically acceptable salt thereof and a bio-degradable polymer material.

As used herein, "donepezil" means a compound of the following Formula 1, and the pharmaceutically acceptable salt of donepezil includes all the salts applicable by those skilled in the art, but may be preferably donepezil hydrochloride:

[Formula 1]

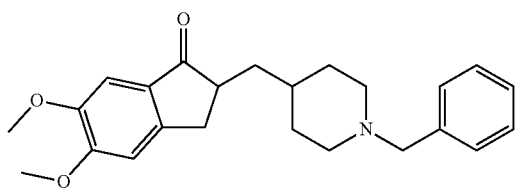

In the composition of the present invention, a weight ratio of the donepezil or the pharmaceutically acceptable salt thereof and the bio-degradable polymer material is 1:1 to 1:5, preferably 1:1.5 to 1:4.

In the present invention, in case of the bio-degradable polymer material, any material may be used without limitation, as long as it may form the microneedle and maintain a shape thereof, and may be also dissolved in vivo after penetrating skin. The bio-degradable polymer material may be, for example, hyaluronic acid or a pharmaceutically acceptable salt thereof, carboxymethyl cellulose, polyvinyl pyrrolidone, polyvinyl alcohol, polylactic glycolic acid, gelatin, collagen, chitosan or mixtures thereof, but is not limited thereto.

In the present invention, an average molecular weight of the bio-degradable polymer material may be 300 to 800 kDa, preferably 500 to 750 kDa.

According to one specific embodiment of the present invention, the bio-degradable polymer material may consist of a mixture of at least one bio-degradable polymer material, and may consist of a mixture of the same polymer materials having different molecular weights.

According to one specific embodiment of the present invention, the bio-degradable polymer material may be hyaluronic acid or a pharmaceutically acceptable salt thereof. An average molecular weight of the hyaluronic acid or the pharmaceutically acceptable salt thereof may be 300 to 800 kDa, preferably 500 to 750 kDa.

In the composition of the present invention, the donepezil or the pharmaceutically acceptable salt thereof is contained by 20 to 43%, preferably by 20 to 38% compared to a total weight of the composition.

Also, in the composition of the present invention, the bio-degradable polymer material is contained by 45 to 80%, preferably by 55 to 65% compared to a total weight of the composition.

According to one specific embodiment of the present invention, the composition of the present invention may be the one dissolved in a hydrophilic solvent. the hydrophilic solvent may be, for example, water, ionic water, physiological saline solution, distilled water, purified water, sterile purified water and $C_{1-4}$ alcohol, but is not limited thereto, and may be preferably water.

The composition for preparing the microneedle of the present invention may further comprise solubilizers, plasticizers, surfactants, preservatives, anti-inflammatory agents, etc. for its purposes.

An intrinsic viscosity of the bio-degradable polymer material used in preparing the composition may be 0.150 to 0.250 m$^3$/kg, preferably 0.160 to 0.230 m$^3$/kg, and more preferably 0.165 to 0.210 m$^3$/kg such that the composition of the present invention may maintain a sufficient strength.

According to the composition for preparing the microneedle of the present invention as above, it is possible to prepare the microneedle, which maintains an appropriate strength for penetrating skin, while having a high donepezil loading capacity.

Soluble Microneedle

The present invention provides a soluble microneedle comprising donepezil or a pharmaceutically acceptable salt thereof and a bio-degradable polymer material; in which a molecular weight of the bio-degradable polymer material is 300 to 800 kDa; and in which a weight ratio of the donepezil or the pharmaceutically acceptable salt thereof and the bio-degradable polymer material is 1:1 to 1:5.

The donepezil or the pharmaceutically acceptable salt thereof and the bio-degradable polymer material comprised in the soluble microneedle of the present invention may be the ones used in the composition for preparing the microneedle of the present invention as they are.

According to one specific embodiment of the present invention, the soluble microneedle of the present invention may be the one prepared in a droplet-born air blowing manner.

The droplet-born air blowing manner includes the following steps:

(1) Spotting a viscous composition containing the donepezil or the pharmaceutically acceptable salt thereof and the bio-degradable polymer material onto a first support and a second support;

(2) Bringing the first support and the second support, with the viscous composition spotted thereonto, into contact with each other;

(3) Distancing the first support and the second support from each other to extend the viscous composition;

(4) Blowing air to the extended viscous composition to dry the same; and (5) Cutting the dried viscous composition to form microneedles.

The preparation method is to use the viscous composition for preparing the microneedle of the present invention as a starting material. The viscous composition forms the microneedle in such a way that such composition is extended while being in contact with the support. Also, the viscous composition, when being inserted into the body, is bio-degradable and a drug is released.

Also, according to one specific embodiment of the present invention, the viscous composition of the step (i) above may be prepared from the following steps:

(i) Dissolving a bio-degradable polymer material in a hydrophilic solvent; and (ii) Adding donepezil or a pharmaceutically acceptable salt thereof into the solution prepared in the step (i).

The spotting of the step (i) above means to discharge the viscous composition in a droplet form. Also, the spotting may be performed with a dispenser, preferably with an air jet dispenser.

In the step (i) above, an amount of the viscous composition per spotting may be 0.1 to 0.24 mg, preferably 0.15 to 0.24 mg.

The first support and the second support may be, for example, selected from hyaluronic acid or a pharmaceutically acceptable salt thereof, carboxymethyl cellulose, polyvinyl pyrrolidone, polyvinyl alcohol, polylactic glycolic acid, gelatin, collagen, chitosan or mixtures thereof, and the first support and the second support may be identical to or different from each other.

The air blowing of the step (4) above may be performed at a wind speed within the range that does not destroy the extended viscous composition. Also, an air blowing time may be appropriately adjusted by those skilled in the art.

The cutting of the step (5) above may be performed in such a way that the dried viscous composition is further distanced or those skilled in the art use an appropriate device.

The droplet-born air blowing manner applied in the present invention may form a microneedle without any additional treatment such as heat, ultraviolet rays or the like, and thus such manner has a low risk of denaturalizing effective components and is also economical with a short time required for preparation.

Also, the droplet-born air blowing manner applied in the present invention does not use a mold and thus remains unaffected by surface tension, and thus is advantageous to applying a bio-degradable polymer having a relatively high molecular weight.

The inventive soluble microneedle prepared as above may efficaciously penetrate skin, when a strength thereof is at least 0.058 N or more. According to a specific embodiment of the present invention, the strength of the inventive soluble microneedle may be 0.10 to 1.40 N, preferably 0.30 to 0.80 N.

In the present invention, a length of the soluble microneedle may be 500 to 950 μm, preferably 650 to 750 μm from the support.

In the present invention, a tip diameter of the soluble microneedle may be 35 to 100 μm, preferably 45 to 85 μm.

In the present invention, a mass of one the soluble microneedle may be 32.5 to 61.5 μg, preferably 40 to 61.5 μg.

The soluble microneedle of the present invention may be used for preventing, treating or alleviating dementia. The dementia may be particularly Alzheimer's dementia, but is not limited thereto.

The soluble microneedle of the present invention may maintain an appropriate strength for penetrating skin, while having a high drug loading capacity, and thus even a small amount of such microneedle may be enough to deliver a sufficient amount of a drug into the body. Also, the soluble microneedle of the present invention is bio-degradable in vivo neither with skin irritation nor with the need for removal, and thus shows a very high compliance with medication and a very high adherence to medication.

Microneedle Percutaneous Patch

The present invention also provides a microneedle percutaneous patch, comprising (a) a soluble microneedle of the present invention; and (b) a support with at least one soluble microneedle attached thereto.

The soluble microneedle is the same as described above, and a detailed description thereof will be omitted hereinafter.

The microneedle patch of the present invention holds the microneedle in one side, and may insert the microneedle into skin by pressurization.

In the present invention, the "support" is a plane layer, to which the microneedle may be attached, and may contain, for example, hyaluronic acid or a salt thereof, carboxymethyl cellulose, polyvinyl pyrrolidone, polyvinyl alcohol, polylactic glycolic acid, gelatin, collagen, chitosan or mixtures thereof, but is not limited thereto. The support preferably contains hyaluronic acid or a salt thereof. Also, the support of the microneedle patch of the present invention may be a material having adhesion.

In the microneedle patch of the present invention, an amount of loading capacity of donepezil or a pharmaceutically acceptable salt thereof per unit area of the support may be 2.2 to 11 ng/mm$^2$, preferably 6.6 to 10 ng/mm$^2$. Here, an area of the support means only a region in the percutaneous patch, to which the soluble microneedle is attached.

Also, in the microneedle patch of the present invention, the number of soluble microneedles per unit area of the support may be 0.2 to 0.5 pieces/mm$^2$, preferably 0.3 to 0.46 pieces/mm$^2$.

Furthermore, in the microneedle patch of the present invention, an interval of soluble microneedles attached to the support may be 0.2 to 0.5 mm, preferably 0.3 to 0.4 mm. The interval of soluble microneedles means a distance between at least two microneedles disposed apart from each other, and is obtained by measuring a linear distance between one microneedle tip and another microneedle tip.

Conventionally, even if the strength of one microneedle is appropriate for penetrating skin, a degree of skin penetration is decreased due to a bed nail effect at too close an interval between microneedles in the microneedle patch. However, the soluble microneedle of the present invention has a high drug loading capacity, and thus just a small number of the soluble microneedles may be enough to deliver an effective amount of the drug into the body. Accordingly, an interval between the soluble microneedles may be disposed to some degree that the bed nail effect does not occur. After all, the soluble microneedle patch of the present invention has a high drug loading capacity, and thus the microneedle patch even with a narrow area may be enough to deliver an effective amount of the drug into the body.

In the microneedle patch of the present invention, an insertion capacity of the soluble microneedle into skin per unit area is 90% or more, preferably 95% or more, and more preferably 99% or more.

Also, the microneedle patch of the present invention has a bioavailability at least 1.5 times more excellent than in the case of orally administering the same dose of the same donepezil or the pharmaceutically acceptable salt thereof.

According to one specific embodiment of the present invention, the microneedle patch of the present invention may take on a structure, in which adhesive sheets are attached onto the supports in one side attached with (c) soluble microneedles and in the other side opposite thereto.

The adhesive sheets may contain, for example, polyurethane, polyethylene, polyester, polypropylene, polyvinyl chloride, hydrocolloid or mixtures thereof.

The microneedle percutaneous patch of the present invention may be used for preventing, treating or alleviating dementia. The dementia may be particularly Alzheimer's dementia, but is not limited thereto.

Advantageous Effects

A composition for preparing a microneedle of the present invention may be used to prepare a soluble microneedle, which shows strength enough to penetrate skin, while having an excellent drug (donepezil) loading capacity.

Also, the soluble microneedle of the present invention may maintain an appropriate strength for penetrating skin, while having a high drug (donepezil) loading capacity, and thus even a small amount of such microneedle may be enough to deliver a sufficient amount of a drug into the body. Furthermore, such soluble microneedle is bio-degradable in vivo with neither skin irritation nor need for removal, and thus shows a high compliance with medication and a high adherence to medication.

In addition, a microneedle percutaneous patch of the present invention enables donepezil, which has been conventionally difficult to be applied, to be given in a form of percutaneous administration, and thus may drastically improve the adherence to medication among patients such as those with dementia, etc., who need percutaneous administration, and also shows a more excellent bioavailability than in the case of oral administration.

MODE FOR INVENTION

Hereinafter, the present invention will be described in more detail through the following examples and experimental examples. However, the following examples and experimental examples are provided only for the purpose of illustrating the present invention, and thus the scope of the present invention is not limited thereto.

Examples 1-9

Preparation of Viscous Composition, Microneedle and Microneedle Patch, Containing Donepezil Hydrochloride (1) Preparation of Viscous Composition A bio-degradable polymer, i.e., hyaluronic acid (average molecular weight of 565 to 677 kDa) was added into water in accordance with an amount thereof described in the following table 1, after which donepezil hydrochloride was added thereto in accordance with an amount described in the following table 1, such that a viscous composition was produced, having an average intrinsic viscosity as described in the following table 2.

TABLE 1

| Component | Example | | | | | | | | |
|---|---|---|---|---|---|---|---|---|---|
| | 1 | 2 | 3 | 4 | 5 | 6 | 7 | 8 | 9 |
| Hyaluronic acid | 1.66 | 2.63 | 4.2 | 4.2 | 1.75 | 2.63 | 2.59 | 3.07 | 4.2 |
| Donepezil hydrochloride | 0.5 | 1.5 | 2.25 | 2.25 | 1.0 | 1.5 | 1.5 | 1.5 | 2.25 |

(Unit: mg)

TABLE 2

| Example | | | | | | | | |
|---|---|---|---|---|---|---|---|---|
| 1 | 2 | 3 | 4 | 5 | 6 | 7 | 8 | 9 |
| 0.17 | 0.195 | 0.195 | 0.195 | 0.165 | 0.165 | 0.193 | 0.195 | 0.195 |

(Unit: $m^3/kg$)

(2) Formation of Microneedle and Patch

The viscous composition prepared with donepezil and the bio-degradable polymer material was extended, after which the extended viscous composition was dried by air blowing. The dried and coagulated viscous composition was cut to prepare microneedles and a patch containing the same (area with the microneedles attached thereto: 226.98 $mm^2$).

TABLE 3

| | Example | | | | |
|---|---|---|---|---|---|
| | 1 | 2 | 3 | 4 | 5 |
| Discharge amount per microneedle | 150 μg | 150 μg | 204 μg | 204 μg | 100 μg |
| Interval of microneedles | 0.3 mm | 0.2 mm | 0.2 mm | 0.2 mm | 0.3 mm |
| Number of microneedles | 70 | 105 | 105 | 105 | 70 |

TABLE 3-continued

| | Example | | | |
|---|---|---|---|---|
| | 6 | 7 | 8 | 9 |
| Discharge amount per microneedle | 150 μg | 150 μg | 171 μg | 240 μg |
| Interval of microneedles | 0.2 mm | 0.2 mm | 0.2 mm | 0.2 mm |
| Number of microneedles | 105 | 105 | 105 | 105 |

Figure 1:
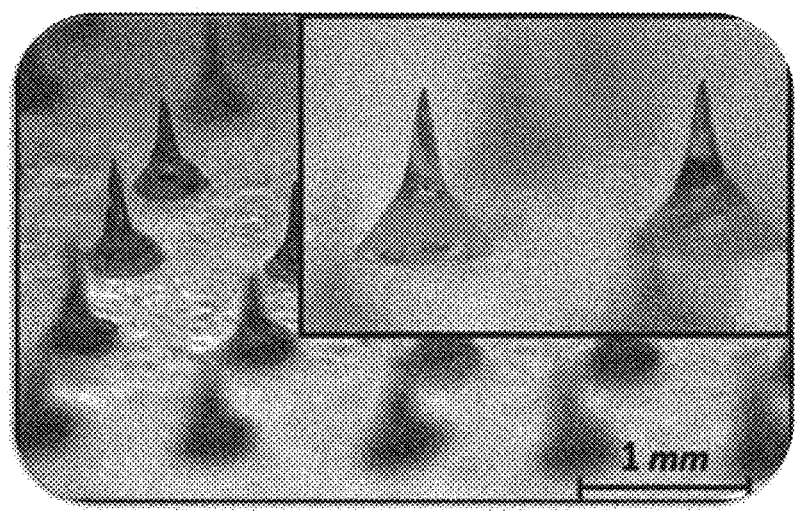
FIG. 1 shows a soluble microneedle of the present invention in a structural view.
Figure 2:
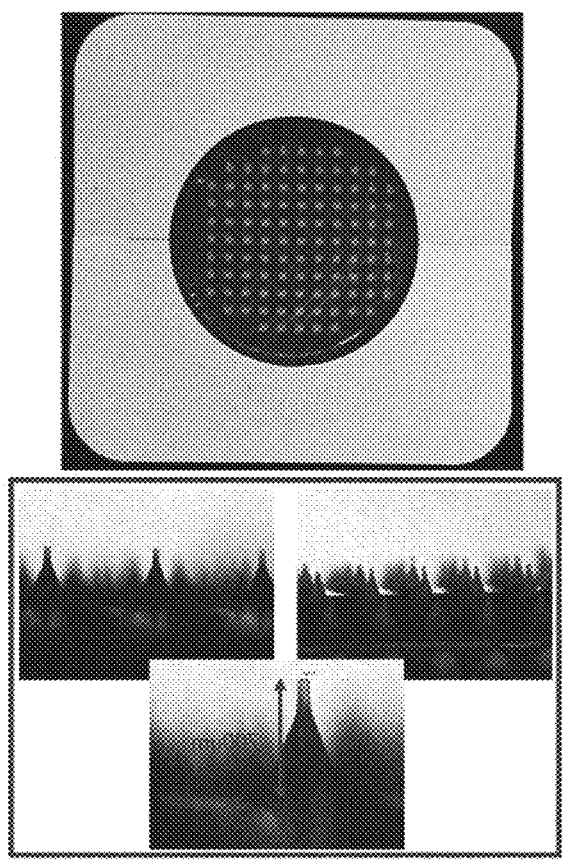
FIG. 2 shows a microneedle patch of the present invention in a structural view.
Figure 3:
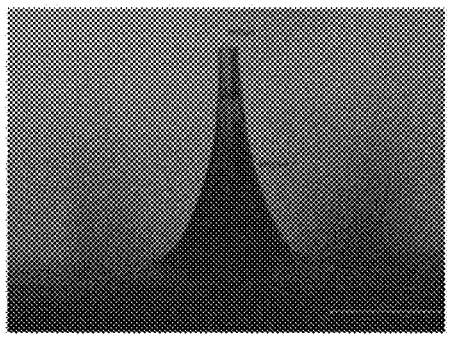
FIG. 3 shows the observation of the microneedles prepared in Examples 1 to 4 in a microscopic view.
Figure 3:
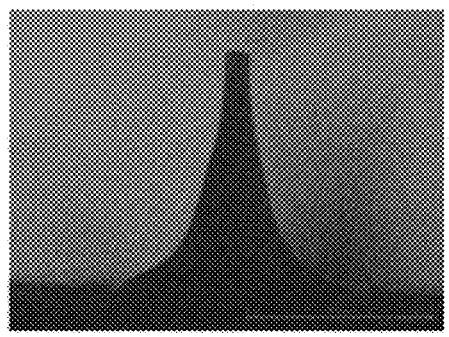
Figure 3:
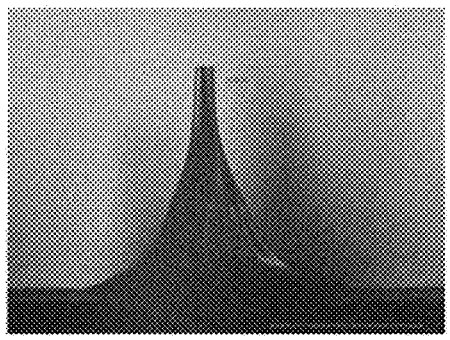
Figure 3:
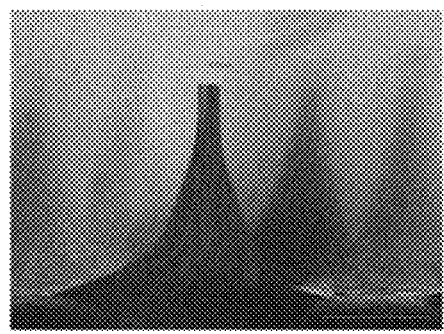

From the results, it was shown that the microneedles are formed as shown in FIG. 3, and a length of the microneedles and a diameter of their tips observed with an optical microscope are the same as shown in the following table 4.

TABLE 4

| | Example | | | | |
|---|---|---|---|---|---|
| | 1 | 2 | 3 | 4 | 5 |
| Length | 650 ± 50 μm | 700 ± 50 μm | 900 ± 50 μm | 700 ± 50 μm | 750 ± 50 μm |
| Tip diameter | 50 ± 20 μm | 60 ± 10 μm | 65 ± 10 μm | 65 ± 10 μm | 80 ± 10 μm |

| | Example | | | |
|---|---|---|---|---|
| | 6 | 7 | 8 | 9 |
| Length | 750 ± 50 μm | 700 ± 50 μm | 700 ± 50 μm | 700 ± 50 μm |
| Tip diameter | 80 ± 10 μm | 60 ± 10 μm | 60 ± 10 μm | 65 ± 10 μm |

Comparative Example

A comparative example was prepared under the conditions of the following table 5, while carrying out the same process as described in Examples above.

TABLE 5

| | | Comparative Example 1 |
|---|---|---|
| Composition | Hyaluronic acid | 56.2% |
| | Donepezil hydrochloride | 43.8% |
| Average intrinsic viscosity | | 0.195 |
| Discharge amount per microneedle | | 150 μg |
| Interval of microneedles | | 0.2 mm |
| Number of microneedles | | 105 |

Experimental Example 1

Measurement of Microneedle Strength

Out of the microneedles attached to a support, a compressive strength for those in the three central parts was measured with a tension and compression tester. With regard to the six samples prepared in the same Examples, strength was repeatedly measured to calculate an average strength value. The strength of the microneedles corresponding to Examples 1 to 9 is the same as shown in the following table 6.

TABLE 6

| Example | | | | | | | | |
|---|---|---|---|---|---|---|---|---|
| 1 | 2 | 3 | 4 | 5 | 6 | 7 | 8 | 9 |
| 0.242 ± 0.038 | 1.121 ± 0.211 | 0.790 ± 0.124 | 0.746 ± 0.118 | 0.962 ± 0.09 | 0.574 ± 0.181 | 0.777 ± 0.135 | 1.32 ± 0.283 | 0.752 ± 0.483 |

(Unit: N)

As above, it may be seen that the microneedle of the present invention shows strength enough to penetrate skin.

Experimental Example 2

Measurement of Skin Insertion Capacity of Microneedle

Figure 4:
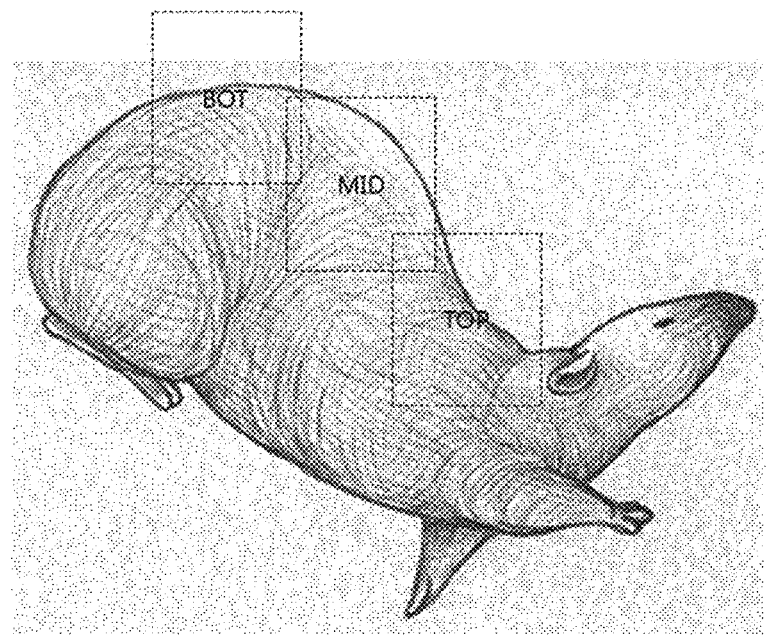
FIG. 4 shows the markings of regions to which the microneedle patch is attached in Experimental Example 1.

An eight-week old male SD rat was divided into bottom (BOT), middle (MID) and top (TOP) parts as shown in FIG. 4, after which the microneedle patches prepared in Example 4 were attached thereto, respectively. In five minutes later, the microneedle patches were removed therefrom, after which the number of holes on the rat skin was observed with an optical microscope, such that an experiment was performed repeatedly three times by means of the same method.

Figure 5:
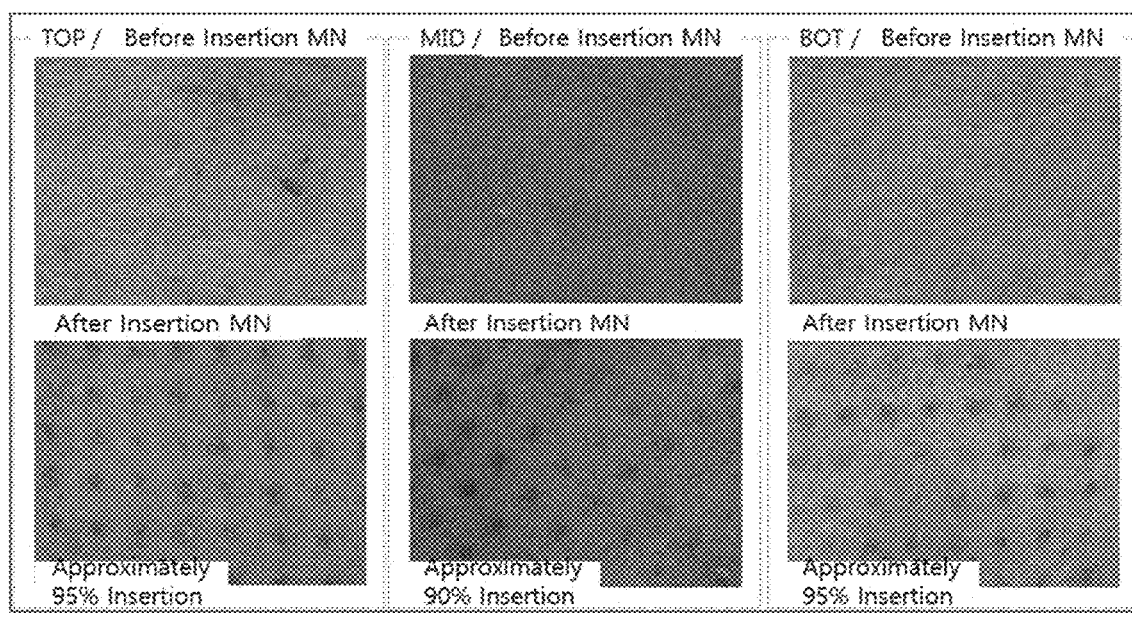
FIG. 5 shows the observation of rat skins in an optical microscopic view before and after the microneedle (MN) is inserted thereinto in Experimental Example 1.

From the results, it might be identified that the microneedle (MN) is inserted by 95% or more as shown in FIG. 5. In other words, it might be seen that the microneedle of the present invention has an appropriate strength for penetrating skin.

Experimental Example 3

Measurement of Donepezil Elution Rate of Microneedle

Figure 6:
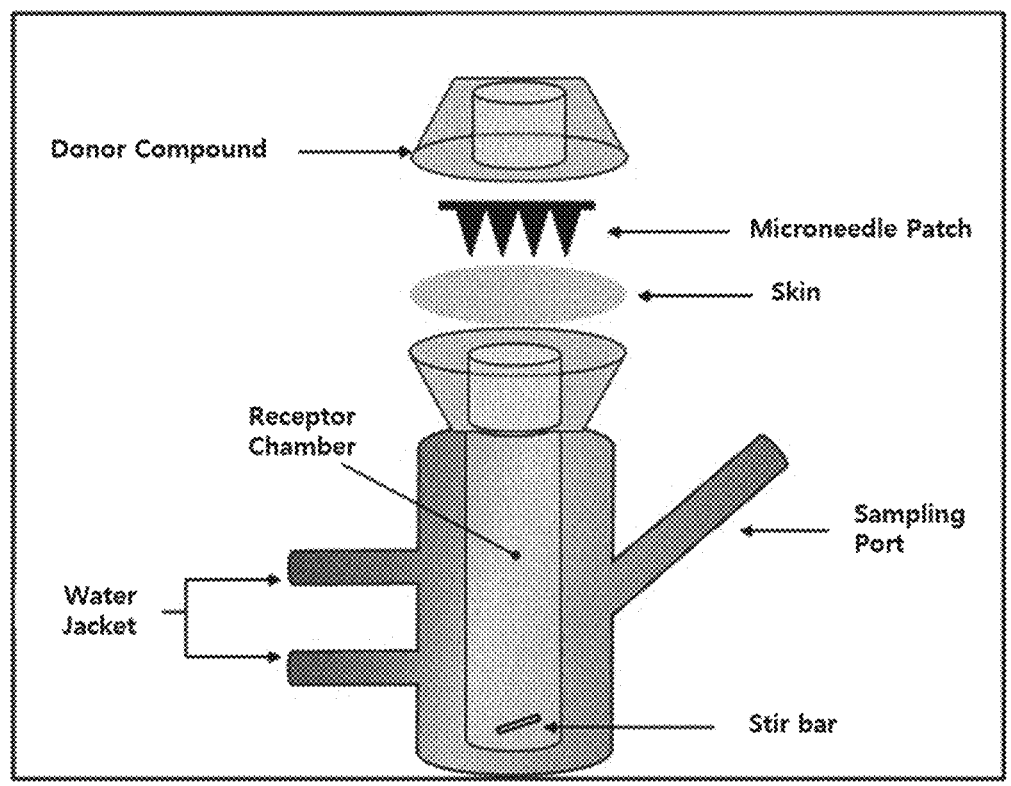
FIG. 6 shows an experimental device used in a Franz diffusion testing method.

A donepezil elution rate of the microneedle patch of the present invention was measured with a Franz diffusion test. The Franz diffusion test is an experiment capable of analyzing a trend of drug elution in skin; is performed with a test device as shown in FIG. 6; and measures an elution rate by identifying an amount of the drug delivered into a receptor chamber after penetrating skin.

The elution rate of donepezil was identified with the microneedle patch of Example 1. Particularly, a refrigerated pig skin was thawed at room temperature, after which the microneedle prepared in Example 1 was applied thereto by using an applicator five times. After that, the pig skin, to which the microneedle prepared in Example 1 was applied, was placed onto the receptor chamber filled with PBS 1×, after which 1 ml thereof was sampled from the receptor chamber at a pre-determined interval of time, and the receptor chamber was supplemented again with 1 ml of PBS 1×. A temperature of water in a water jacket was kept at 37° C. in order to constantly maintain a temperature of the receptor chamber. At the end of the experiment, the microneedle was removed from the pig skin and observed with a microscope, in order to look into a remaining shape of the microneedle. With regard to the sample collected from the receptor chamber, an elution rate was analyzed at an initial value of the patch by using HPLC.

Figure 7:
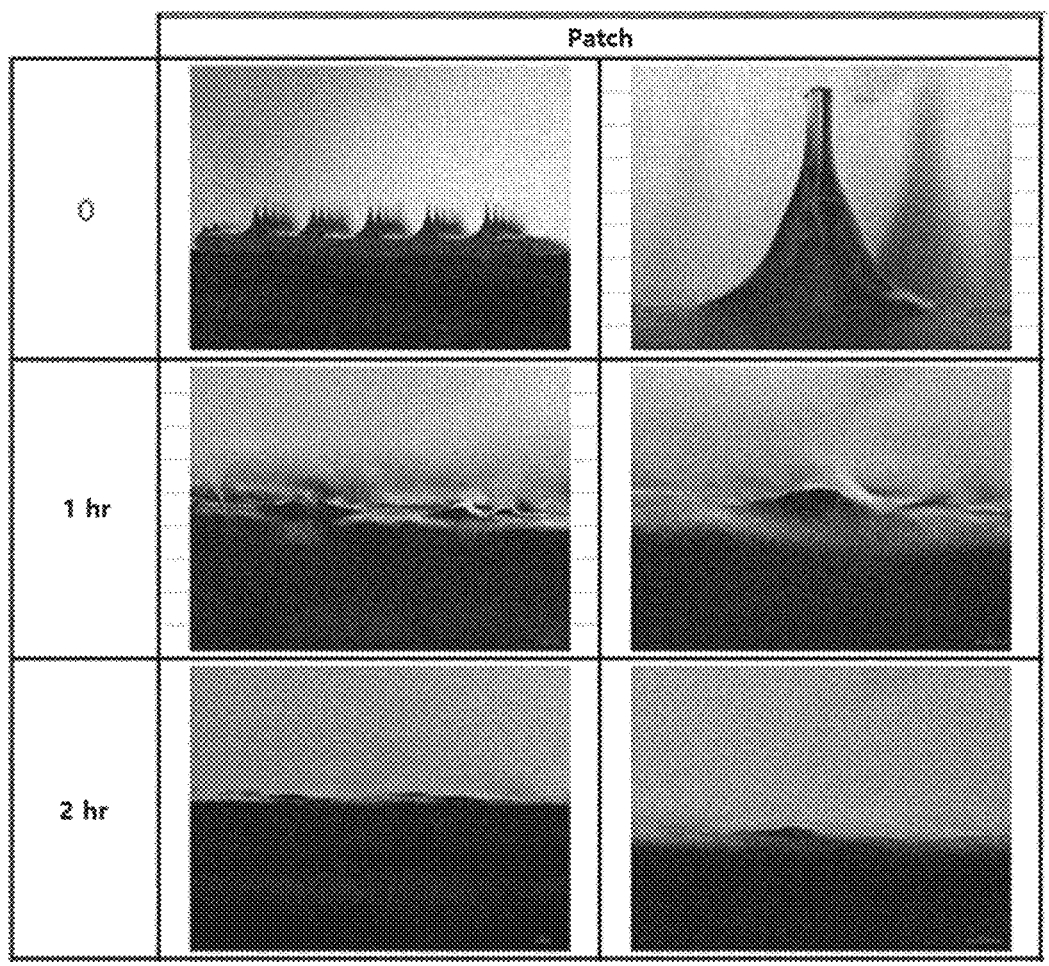
FIG. 7 shows the observation of microneedle shapes with time in the microneedle patch used in Experimental Example 3.
Figure 8:
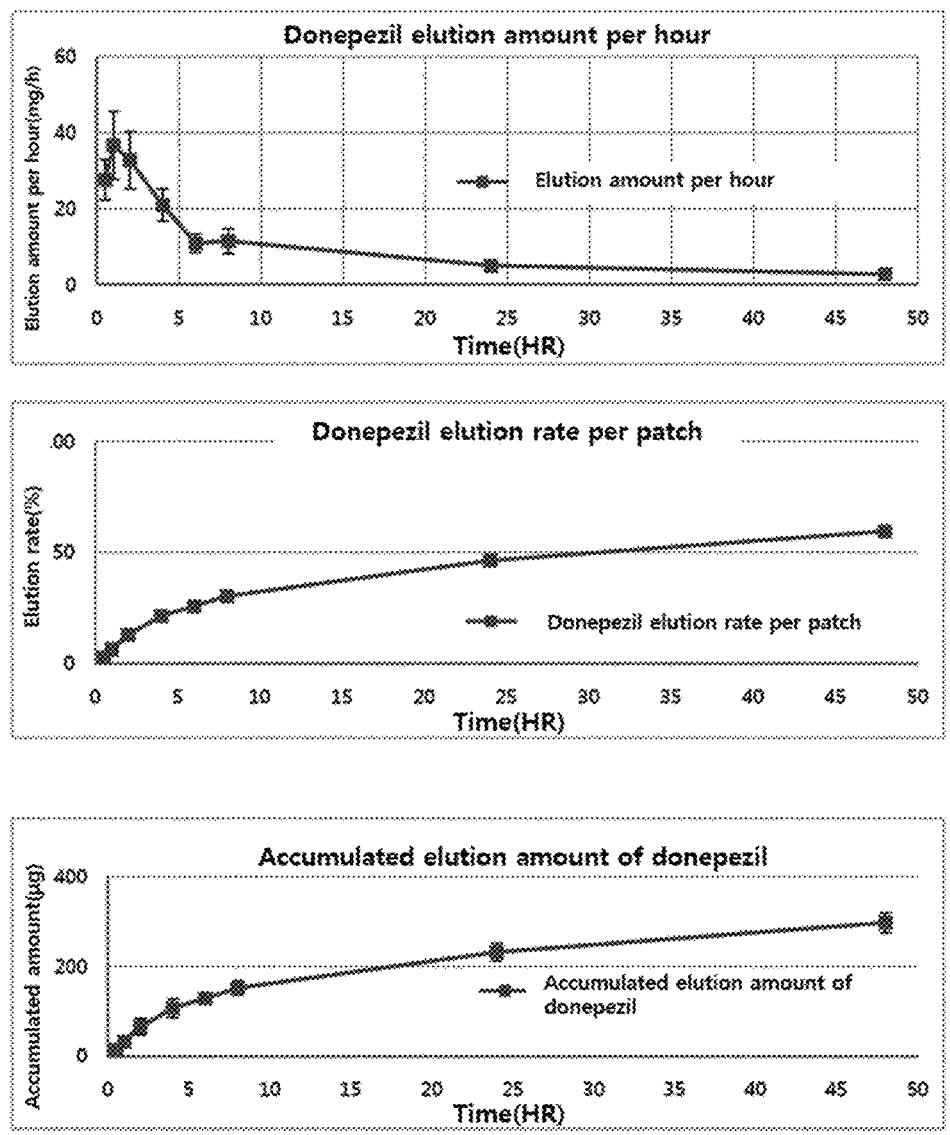
FIG. 8 shows the results of measuring an elution rate of donepezil in Experimental Example 3 in a graphic view, in which (a) is an elution amount of donepezil per hour; (b) is an elution rate of donepezil per patch; and (c) is an accumulated elution amount of donepezil.

From the results, a shape of the microneedle was not observed any more with an elapse of two hours after attaching the microneedle patch as shown in FIG. 7. Also, it was identified that donepezil is eluted by 40.88±6.85% in 24 hours later and eluted by 57.74±3.74% in 48 hours later as shown in FIG. 8. In other words, it may be seen that the microneedle of the present invention is bio-degradable and efficaciously elutes donepezil in vivo.

Experimental Example 4

Identification of Donepezil PK Profile of Microneedle Patch

The microneedles prepared in Examples 3 and 4 respectively were inserted into the shaved eight-week old male SD rats, after which blood was collected therefrom in 0.25, 0.5, 1, 2, 4, 6, 8, 11, 24, 32 and 48 hours later. Also, the same amount of donepezil hydrochloride as that of donepezil hydrochloride contained in the microneedle was suspended/dissolved in purified water and was orally administered, after which blood was collected in 0.17, 0.33, 0.671, 2, 4, 8 and 24 hours later. A blood sample was subjected to centrifugation, after which serum was obtained and analyzed by LC/MS/MS to calculate pharmacokinetic parameters.

From the results, it may be seen that the microneedle of the present invention shows bioavailability about 2.0 to 2.5 times more excellent than in the case of oral administration as shown in the following table 7. Thus, the microneedle of the present invention may deliver donepezil more efficiently than in the case of oral administration.

TABLE 7

| Dosage form | $T_{1/2}$ | $T_{max}$ | $C_{max}$ | AUC |
|---|---|---|---|---|
| Example 4 (n = 7) | 8.8 ± 2.2 | 4 ± 1.1 | 163 ± 25.9 | 2024 ± 275 |
| Example 3 (n = 7) | 15.4 ± 6.3 | 5.5 ± 2.6 | 73 ± 16 | 1591 ± 313 |
| Oral (n = 10) | 3.7 ± 1.1 | 0.93 ± 0.75 | 90.9 ± 27.9 | 815 ± 163 |

Experimental Example 5

Evaluation of Optimum Content of Donepezil Contained in Microneedle

The microneedles of Examples 1 to 9 and the microneedle of Comparative Example 1 were kept at room temperature, in order to measure an optimum content of donepezil which may be stably contained therein.

In Comparative Example 1, in which a content of donepezil in the microneedle is 43.8%, the precipitation of donepezil was identified with an elapse of three days later, and thus it was determined that there may occur a problem of preparation homogeneity. Also, a decline in strength and insertion capacity was observed, too. On the other hand, in case of the microneedles of Examples 1 to 9, in which a content of donepezil is 23.0 to 37.8%, the precipitation of donepezil was not observed, but a decline in strength and insertion capacity was observed. On contrary, in case of the microneedles of Examples 1 to 9, in which a content of donepezil is 23.0 to 37.8%, the precipitation of donepezil was not observed.

Thus, it may be seen that an appropriate content of donepezil in the microneedle is 43% or less, more preferably 38% or less.

INDUSTRIAL APPLICABILITY

A soluble microneedle of the present invention has an excellent strength, while having a high drug (donepezil) loading capacity, and thus may contain an effective amount of donepezil or a pharmaceutically acceptable salt thereof even with a small area of the microneedle. Thus, the present invention produces a lower level of skin irritation and is economical. Furthermore, such soluble microneedle is bio-degradable in vivo with neither skin irritation nor need for removal, and thus shows a high compliance with medication and a high adherence to medication.

In addition, a microneedle percutaneous patch of the present invention enables donepezil, which has been conventionally difficult to be applied, to be given in a form of percutaneous administration, and thus may drastically improve the adherence to medication among patients such as those with dementia, etc., who need percutaneous administration, and also shows a more excellent bioavailability than in the case of oral administration.

Thus, the present invention may be valuably utilized for treating dementia.

The invention claimed is:

1. A soluble microneedle comprising a homogeneous composition of donepezil or a pharmaceutically acceptable salt thereof and hyaluronic acid or a pharmaceutically acceptable salt thereof,
   wherein a weight ratio of the donepezil or the pharmaceutically acceptable salt thereof and the hyaluronic acid or a pharmaceutically acceptable salt thereof, is 1:1.5 to 1:2.05;
   wherein the content of the donepezil or the pharmaceutically acceptable salt thereof is 43 wt % or less of the total weight of the composition.

2. The soluble microneedle according to claim 1, having a strength between 0.058 N and 1.603 N.

3. The soluble microneedle according to claim 2, wherein the strength is between 0.1 N and 1.603 N.

4. The soluble microneedle according to claim 1, having a length of between 500 and 950 pm from a support.

5. The soluble microneedle according to claim 1, having a tip diameter of between 35 and 110 µm.

6. A microneedle percutaneous patch, comprising (a) the soluble microneedle according claim 1; and (b) a support with at least one soluble microneedle attached thereto.

7. The microneedle percutaneous patch according to claim 6, wherein the loading capacity of donepezil or a pharmaceutically acceptable salt thereof per unit area of the support is 2.2 to 11 ng/mm$^2$.

8. The microneedle percutaneous patch according to claim 6, wherein the number of soluble microneedles per unit area of the support is 0.2 to 0.5 pieces/mm$^2$.

9. The microneedle percutaneous patch according to claim 6, wherein the soluble microneedles are attached to the support at an interval of 0.2 to 0.5 mm.

10. The microneedle percutaneous patch according to claim 6, wherein the insertion capacity of the soluble microneedle into skin per unit area is 90% or more.

11. The soluble microneedle according to claim 1, wherein the donepezil or the pharmaceutically acceptable salt thereof does not precipitate in the microneedle.

12. The soluble microneedle according to claim 1, wherein the intrinsic viscosity of the hyaluronic acid or a pharmaceutically acceptable salt thereof is 0.150 to 0.250 m$^3$/kg.

13. The soluble microneedle according to claim 1, wherein the hyaluronic acid or a pharmaceutically acceptable salt thereof is 45 to 80% of the total weight of the composition.

* * * * *